United States Patent [19]

Boyd et al.

[11] Patent Number: 5,340,723
[45] Date of Patent: Aug. 23, 1994

[54] METHOD FOR DIAGNOSING FOR ANEURYSMS

[75] Inventors: Charles D. Boyd, Princeton; Susan B. Deak, Somerset, both of N.J.

[73] Assignee: University of Medicine & Dentistry of New Jersey, Piscataway, N.J.

[21] Appl. No.: 869,745

[22] Filed: Apr. 16, 1992

[51] Int. Cl.⁵ .................. C12Q 1/02; C12Q 1/00; G01N 33/53; C12N 5/00

[52] U.S. Cl. .................................. 435/29; 435/4; 435/7.21; 435/35; 435/240.2; 435/244; 436/63

[58] Field of Search ............... 435/4, 29, 356, 35, 435/7.21, 240.2, 244; 436/63, 86; 530/842

[56] References Cited

PUBLICATIONS

Deak, et al. J of Vascular Surgery pp. 926–927.
Superti-Furga, et al. Human Genetics 82: 104–108 (1989).
Prockop, et al. Amer. J Medical Genetics 34 pp. 60–67 (1989).
Deak, et al. Matrix, vol 12, pp. 92–100 1992.
Deak, et al. Journal of Biological Chemisty vol. 258, No. 241 pp. 15192–15197 1993.
Bruckner, et al. Analytical Biochemisty vol. 110 pp. 360–368 (1981).
Johansan, et al. JAMA vol. 256 No. 14, pp. 1934–1936.
Stolle, et al. J Biol Chemistry. vol. 260 No. 3 pp. 1937–1944 (1985).

*Primary Examiner*—Michael G. Witshyn
*Assistant Examiner*—Jane A. Williams
*Attorney, Agent, or Firm*—Richard R. Muccino

[57] ABSTRACT

The present invention pertains to a method for diagnosing for an aneurysm in a patient which comprises the steps of (a) explanting a skin section containing dermal fibroblast from the patient; (b) culturing the fibroblast to confluence in a culture medium; (c) incubating the cultured fibroblast with labeled proline to provide labeled procollagen in the culture medium; (d) separating the culture medium from the labeled procollagen and treating the labeled procollagen with a solution of protease inhibitor; (e) separating and purifying the labeled procollagen from the solution of protease inhibitor; (f) subjecting the labeled procollagen to protease digestion specific for non-collagenous proteins to form a collagenous mixture; (g) analyzing the collagenous mixture for the ratio of type I collagen to type III collagen; (h) analyzing a control collagenous mixture for the ratio of type I collagen to type III collagen; and (i) comparing the ratio of type I collagen to type III collagen in the collagenous mixture of step (g) to the control mixture of step (h), respectively.

6 Claims, No Drawings

METHOD FOR DIAGNOSING FOR ANEURYSMS

BACKGROUND OF THE INVENTION

1. Field of the Invention

This invention relates to a method for diagnosing for abnormalities in the biosynthesis of type III procollagen in cultured skin fibroblasts. More particularly, this invention relates to a method for diagnosing for aneurysms which comprises incubating cultured fibroblasts with labeled proline to form labeled procollagen, subjecting the labeled procollagen to pepsin digestion, and determining the ratio of type I collagen to type III collagen in the mixture.

2. Description of the Background

The disclosures referred to herein to illustrate the background of the invention and to provide additional detail with respect to its practice are incorporated herein by reference. For convenience, the disclosures are referenced in the following text and respectively grouped in the appended bibliography.

Aneurysms are sacs formed by the dilatation of the wall of an artery, a vein, or the heart. Based on post mortem examinations, 4.5% to 6.6% of the population has an abdominal aortic aneurysm (Fievez, 1989). The underlying causes of aneurysm development are not known, although atherosclerosis, hypertension, and smoking have been suggested as possible factors which either cause or aggravate the development of the disease. In addition, a clear genetic predisposition to the development of aneurysms has been demonstrated in some patients (Johansen and Koepsell, 1986; Tilson add Seashore, 1984 a; b; Cole et al., 1989; Bengtsson et al., 1989, Darling et al., 1989).

Aneurysmal dilatations are commonly seem among the elderly. However, a variety of mutations in the primary structure of type III procollagen can lead to aneurysms in young adulthood (Superta-Furga et al., 1988; Tromp et al., 1989; Kontusaari et al., 1990; and Kontusaari et al., 1990), as demonstrated by the genetic mutations responsible for the rare disorder Ehlers Danlos syndrome IV (EDS IV). Many of the genetic mutations seen in EDS IV patients are associated with alterations in the steady state levels, thermal stability, or secretion of the type III procollagen synthesized by cultured skin fibroblasts (Superta-Furga et al., 1989; Stolle et al., 1985).

The pathogenesis of arterial aneurysms is likely to be multifactoral. Structural alterations in lamellar architecture (Zatina et al., 1984), altered protease levels (Busuttil et al., 1980; Busittil et al., 1982), copper deficiency (Tilson, 1982), elastin abnormalities (Keeley et al., 1989), and hemodynamic factors (Zarins and Glagov, 1982) have all been implicated in the etiology of aneurysms.

In addition, familial clustering of aneurysms (Johansen and Koepsell, 1986, Tilson and Seashore 1984 a; b) suggests that in some patients a heritable factor is involved. Approximately 19% of abdominal aortic aneurysm patients have a documented family history of the disease (Johansen and Koepsell, 1986). However, the number of individuals with a genetic predisposition to the disease may be much greater (Pope et al., 1983; Tilson, 1990).

Mutations in collagen genes may play a role in diseases such as aneurysms (Prockop and Kivirikko, 1984; Prockop, 1985) and several investigators have reported a reduction of type III collagen in skin and pepsin digested media from cultured skin fibroblasts of some patients with cerebral aneurysms (Poe et al., 1981; Neil-Dwyer et al., 1983; de Paepe et al., 1988). A decreased type III collagen content of the aortic wall of patients with a family history of abdominal aortic aneurysms has also been reported (Menashi et al., 1987). Other reports, however, have shown no significant alterations in either the synthesis or quantity of type III collagen associated with non EDS IV related aneurysms. For example, normal biosynthesis of type III procollagen has been demonstrated by cultured skin fibroblasts from a proband in a family with three members having cerebral aneurysms (Leblanc et al., 1989). Similarly, the type III collagen content of the aortic walls of abdominal aortic aneurysm patients, either with or without a family history of the disease, were found to be comparable to age matched controls (Rizzo et al., 1989).

Proteolytic enzymes have been reported to be useful as probes for the triple-helical conformation of procollagen. These enzymes digest all nonhelical regions in triple-helical collagen molecules as well as non-collagenous molecules (Bruckner et al., 1981).

Patients with the bone disorder osteogenesis imperfecta have been found to secrete a type I procollagen which lacked pro-alpha2(I) chains and consisted of a trimer of pro-alpha1(I) chains (Deak et al., 1983). The pro-alpha2(I) chains were postulated to have a mutated structure in the carboxyl-terminal propeptides reducing their affinity to form trimers with the pro-alpha2(I) chains. The trimer of pro-alpha1(I) chains was found to have decreased thermal stability presumably due to the absence of pro-alpha2(I) chains (Deak et al., 1985).

In a study on 10 patients with the connective tissue disorder Ehlers-Danlos type IV syndrome (EDS IV), 9 patients were found to secrete a decreased amount of type III procollagen and one patient was found to secrete a structurally altered type III procollagen (Stolle et al., 1985).

DNA tests for mutations in the type III procollagen were reported to be helpful to identify individuals at risk for familial aortic aneurysms (Kontusaari et al., 1990).

SUMMARY OF THE INVENTION

The present invention pertains to a method for diagnosing for an aneurysm in a patient which comprises the steps of:

(a) explanting a skin section containing dermal fibroblast from the patient;

(b) culturing the fibroblast to confluence in a culture medium;

(c) incubating the cultured fibroblast with labeled proline to provide labeled procollagen in the culture medium;

(d) separating the culture medium from the labeled procollagen and treating the labeled procollagen with a solution of protease inhibitor;

(e) separating and purifying the labeled procollagen from the solution of protease inhibitor;

(f) subjecting the labeled procollagen to protease digestion specific for non-collagenous proteins to form a collagenous mixture;

(g) analyzing the collagenous mixture for the ratio of type I collagen to type III collagen;

(h) analyzing a control collagenous mixture for the ratio of type I collagen to type III collagen; and (i) comparing the ratio of type I collagen to type III collagen in the collagenous mixture of step (g) to the control mixture of step (h), respectively.

DETAILED DESCRIPTION OF THE INVENTION

In accord with the present invention, the synthesis of collagenous proteins by cultured skin fibroblasts taken from 14 patients was examined to determine whether abnormalities in the biosynthesis of type III procollagen, indicative of structural mutations in the gene (*Prockop et al.,* 1989; *Byers,* 1990), could be detected. The 14 unrelated patients, undergoing corrective surgery for common "atherosclerotic" abdominal aortic aneurysms, had an abdominal aortic aneurysm and either an aneurysm at a second site (8 patients) or a first order relative with an abdominal aortic aneurysm (6 patients). Clinically relevant symptoms in these patients were detected in the 6th or 7th decade of life.

Fibroblasts were labeled with $^3$H-proline and following pepsin digestion of media proteins, the ratio of type I/III collagen was examined by denaturing polyacrylamide gel electrophoresis (SDS-PAGE). With the exception of two patients, the ratio of type I/III collagen in the media of fibroblasts from aneurysm patients was similar to control values (6 controls). In two of the patients, the type I/III collagen ratio was >3 standard deviations from the mean of both control ratios and those of other aneurysm patients. mRNA levels coding for type III procollagen, however, were normal in both patients. Patient no. 1 showed reduced type III procollagen on SDS-PAGE analysis of intracellular proteins, possibly due to decreased translation of the mRNA coding for type III procollagen. Intracellular and media type III procollagen levels were normal in patient no. 2 but media type III collagen was reduced by over 50% after digestion with a combination of trypsin and alpha-chymotrypsin for 5 minutes at 36° C. Control type III collagen was only reduced after digestion at 39° C. This data suggests an altered thermal stability of the type III collagen trimer synthesized by this patient, probably due to a mutation in the amino acid sequence. Although the genetic basis for the development of aneurysms is complex, some forms of the disease may be caused by mutations in the gene coding for type III procollagen.

These results demonstrate normal biosynthesis of type III procollagen by fibroblasts from six patients with a documented family history of abdominal aortic aneurysms. Among patients with multiple aneurysms, fibroblasts from six out of eight patients also displayed normal synthesis of type III procollagen. Clearly, the majority of abdominal aortic aneurysm patients in this study had no detectable defect in type III procollagen, suggesting that pervasive mutations in that protein will be predominantly characteristic of EDS IV aneurysms (*Nicod et al.,* 1989; *Powell et al.,* 1987).

These findings show that detectable alterations in type III procollagen biosynthesis are not always associated with aneurysms but that some abdominal aortic aneurysm patients with functionally important defects in the structure or synthesis of type III procollagen can be identified. The two patients demonstrating type III collagen deficiency clearly had different abnormalities in the biosynthesis of the protein, suggesting that unrelated individuals will have different mutations in the gene. Although a causal relationship between mutations in type III collagen and the development of "atherosclerotic" aortic aneurysms has not been established, this study helps define the probable number of abdominal aortic aneurysm patients with functionally important alterations in the biosynthesis or structure of type III procollagen. The data presented suggest that a fractional but nonetheless notable proportion of abdominal aortic aneurysms may arise from mutations in the gene coding for type III procollagen. Hence, the method of the present invention provides a means for diagnosing for an aneurysm or the potential for an aneurysm.

Since neither of the two patients showing abnormal biosynthesis of type III procollagen had a family history of clinically relevant abdominal aortic aneurysms, a sporadic mutation in the type III procollagen gene may have occurred. More importantly, however, in a multifactoral disease characterized by complex inheritance, late onset of symptoms, and modulation by environmental factors, a familial tendency to the disease may be masked in these and other patients.

The multifactoral pathogenesis of arterial aneurysms and familial clustering of aneurysms, coupled with the known association of defects in the type III procollagen gene with aneurysm formation in the rare autosomal dominant disorder EDS IV, prompted us to investigate the biosynthesis of type III procollagen by fibroblasts from patients with "atherosclerotic" aortic aneurysms. Abnormalities in type III procollagen biosynthesis by cultured skin fibroblasts would reflect mutations in the gene (*Prockop and Kivirikko,* 1985) and not environmental or in situ arterial conditions. Therefore, we focused on patients with a history of aneurysms in a first order relative and to those with aneurysms at multiple loci. In general, the types of aneurysms which may be diagnosed according to the method of the present invention are arterial aneurysms such as abdominal aneurysms and cerebral aneurysms. Preferably, the type of aneurysm to be diagnosed is an abdominal aneurysm.

In general, the method for diagnosing for an aneurysm in a patient comprises explanting a skin section containing dermal fibroblast from the patient either by punch biopsy or by surgical incision. The fibroblasts are then cultured to confluence in a culture medium such as Dulbecco's Minimal Essential Medium. The cultured fibroblasts are then incubated with labeled proline to incorporate the labeled proline into labeled procollagen in the culture medium. Suitable types of labeled proline which may be employed include radiolabeled prolines such as $^3$H-proline and $^{14}$C-proline. Preferably the labeled proline is $^3$H-proline. The culture medium is then separated from the labeled procollagen, such as by decantation, and the labeled procollagen is then treated with a solution of protease inhibitor to inhibit any non-specific degradation. Examples of protease inhibitors which may be employed include N-ethylmaleimide and p-aminobenzamidine. The labeled procollagen is then separated from the solution of protease inhibitor such as by precipitation with ammonium sulfate and centrifugation. The labeled procollagen is then purified and separated from excess ammonium sulfate such as by dialysis. The labeled procollagen is then subjected to protease digestion specific for non-collagenous proteins such as pepsin, trypsin, or alpha-chymotrypsin digestion to form a protease-resistant collagenous mixture. The collagenous mixture is then analyzed to determine the ratio of type I collagen to type III collagen. The collagenous mixture may be analyzed by such methods as denaturing polyacrylamide gel electrophoresis, immunoprecipitation, and western blotting, and preferably by denaturing polyacrylamide gel electrophoresis. The ratio of type I collagen to type III collagen in the test sample of collagenous mixture is then compared to the corresponding ratio in a control mixture to determine the likelihood of an aneurysm developing in the patient.

In general, the ratio of type I collagen to type III collagen in a control sample should range from about 6 to about 9. The ratio of type I collagen to type III collagen in a test sample considered abnormal and indicative of an aneurysm will range from about 12 to about 38.

The present invention is further illustrated by the following examples which are not intended to limit the effective scope of the claims. All parts and percentages in the examples and throughout the specification and claims are by weight of the final composition unless otherwise specified.

EXAMPLES

Reagents and Chemicals

Molecular biology grade reagents were obtained from International Biotechnologies, Inc, New Haven Conn., or Pharmacia Fine Chemicals, Uppsala, Sweden. Enzymes and enzyme inhibitors were purchased from Sigma Chemical Co., St. Louis, Mo.

Cell Culture

Dermal fibroblasts were explanted from small pieces of skin obtained either from a punch biopsy or a surgical incision. The procedure for obtaining skin specimens was approved by the Institutional Review Board and informed consent was obtained from each donor.

Culture conditions were similar to those previously described (Deak et al., 1983). Media, fetal calf serum, glutamine and antibiotics were obtained from Flow Laboratories, McLean, Va. Cells were grown in the presence of 50 ug/ml ascorbate. Following trypsin digestion, cells were passaged by splitting one flask into three. Confluent cells were labeled at passages 3–7. RNA was extracted from cells at passage 7–8.

Patient Population

Cultured skin fibroblast strains from 14 unrelated individuals (average age 65.6+/−1.6, SEM) undergoing corrective surgery for an abdominal aortic aneurysm were established. Three of the patients were female. Six of the patients had an abdominal aortic aneurysm and a first degree relative, mother, father, brother, or sister who had either died from, or had corrective surgery for, an abdominal aortic aneurysm. Eight of the patients did not have a family history of aneurysms, but an aneurysm at a second site (three thoracic aneurysms, three popliteal aneurysms, one recurrent abdominal aortic aneurysm, and one patient with arteriomegaly).

Four control cell strains were also established from apparently normal donors aged 6 months, 6 years, 43 years, and 63 years. Two control cell strains (CRL 1510, CRL 1521) were obtained from American Type Culture Collection (Rockville, Md.). No variation in type I/III collagen ratios greater than 3 standard deviations from the mean of the ratio for controls was observed associated either with age or passage number.

Labeling of Procollagen

Fibroblasts were grown in 25 cm$^2$ flasks. After the fibroblasts reached confluence, they were metabolically labeled for 18 hours in medium containing antibiotics, vitamin C (50 ug/ml), glutamine (2 mM), and 50 uCi/ml of L-(2,3,4,5-$^3$H) proline, 102 Ci/mM obtained from Amersham International, Arlington Heights, Il. Media samples were processed as previously described (Deak et al., 1983). Briefly, the media was decanted and placed on ice. A cocktail of proteinase inhibitors consisting of 25 mM EDTA, 1mM N-ethylmaleimide, 10 mM p-aminobenzamidine, 1mM phenylmethylsulfonylfluoride was added, and the media proteins precipitated by the addition of 176 mg/ml of ammonium sulfate. The samples were gently agitated at 4° C. overnight. The media proteins were recovered by centrifugation for 30 minutes at 13,000×g at 4° C. in a microcentrifuge. Labeling and processing of intracellular procollagens were performed as described previously (Deak et al., 1983).

Determination of I/III Collagen Ratios

Cultured skin fibroblasts were metabolically labeled with $^3$H-proline for 18 hours. Collagenous proteins contain approximately seven times more proline than do other proteins. Therefore, labeling with $^3$H-proline results in the predominant incorporation of label into collagenous protein. Pepsin digestion further selects for collagenous proteins, since other proteins are sensitive to proteolysis while the triple helical domains of structurally normal type I and III collagen are resistant to enzymatic digestion at temperatures below 42° C. and 39° C., respectively (Superta-Furga et al., 1989, Deak et al., 1985). The carboxyl and amino propeptides of procollagen, however, are removed by proteolysis.

Prior to pepsin digestion, the ammonium sulfate pellets of media proteins were resuspended in 0.4 M NaCl in 0.1 M Tris-HCl, pH 7.4 at 4° C. The proteins were then dialyzed against 0.1 N acetic acid and digested for 2 hours at 15° C. with 100 ug/ml of pepsin. Following digestion, 1 ug/ml of pepstatin was added and the samples left on ice for 30 minutes. The samples were then added to boiling sodium dodecyl sulfate (final concentration 2%) and heated to 100° C. for 5 minutes. The samples were adjusted to a final concentration of 0,125 M Tris-HCl, pH 6.8, 10% glycerol, 0.005% bromophenol blue for polyacrylamide gel electrophoresis (SDS-PAGE) under non-reducing conditions.

The triple helical domain of type I collagen does not contain disulfide bonds. Under non-reducing conditions of electrophoresis, the individual alpha chains will be separated. By contrast, type III collagen has two disulfide bonds near the carboxy terminus of the collagen helical domain. Under non-reducing conditions, therefore, type III collagen migrates as a disulfide bonded trimer. To prevent inadvertent reduction of disulfide bonds, electrophoresis plates and combs were soaked in a dilute solution of iodoacetamide for 30 minutes prior to assembly of the gel. The SDS-PAGE gels consisted of 4% stacking and 5% separating gels and electrophoresis was performed at 50 V overnight. Conditions of electrophoresis and processing of gels were as described earlier (Deak et al., 1983). X-ray film (DuPont cronex) was placed on the processed gels and both secured in a cassette at −70° C. for 2–5 days. Relative intensities of protein bands were quantified using the Helena quick scan densitometer (Helena Laboratories, Beaumont, Tex.). Linearity of exposure times was determined by comparison of the ratio of alpha1(I) to alpha2(I) collagen bands following different exposure times of the X-ray film. A ratio of approximately 2:1 for these peptides was used as a standard for exposure time for each sample.

Assay for Thermal Stability of Type III Collagen

Digestion of media procollagens with a combination of trypsin and alpha-chymotrypsin was performed as describe earlier (*Deak et al.,* 1985) except that the digestion times were 5 minutes and not 10 minutes. Quantitation of collagenous proteins was performed as described above.

Analysis of mRNA

Northern blot analysis of total RNA and slot blot quantitation of oligo dT purified RNA were performed as described previously (*Pierce et al.,* 1987). Nick translation of DNA coding for the carboxyl propeptide domain of type I or III procollagen was performed using a commercially available kit (Boeringer-Mannheim, Mannheim, W. Germany) and $^{32}$P-dCTP, 3000 Ci/mM, (ICN, Irvine, Calif.). An Eco RI /Xho I subclone of T3-I, a cDNA coding for type III procollagen (The genes coding for elastin and type III collagen are located on different regions of the long arm of chromosome 2) and an Eco RI/Ava I subclone of Hf-677 (*Chu et al.,* 1982), a cDNA clone coding for alpha1(I) procollagen (kindly provided by Dr. Darwin J. Prockop, Thomas Jefferson Medical School, Philadelphia, Pa.) were used to determine RNA ratios of type I and III procollagen from serial dilutions of 100–500 ng of poly A+ RNA. The two cDNA fragments cover corresponding regions of the carboxyl propeptide sequences in the two mRNAs. To determine the mRNA ratios, the signal intensities were adjusted for probe size and specific activity. Filter bound radioactive probe was quantified with an AMBIS beta-scanner (San Diego, Calif.) as described previously (*Pierce et al.,* 1987).

Ratios of Type I/III Media Collagen

Non-reduced SDS-PAGE gels were used to quantify the ratios of type I/III collagen with the Helena quick scan densitometer. The ratios of type I/III collagen in controls and aneurysm patients are presented in below Table 1.

TABLE 1

| Ratios of Pro alpha1(I)/Pro alpha1(III) Collagen | |
|---|---|
| Control Patients | 9.30 +/− 1.68, N = 6* |
| Aneurysm Patients | 6.03 +/− 1.13, N = 12* |
| ME | 31 |
| HR | 44 |

*MEAN +/− SEM, no statistically significant difference between two groups.

Table 1 shows the ratio of alpha1(I)/alpha1(III) procollagens from the media of cultured skin fibroblasts from 6 control patients and 14 abdominal aortic aneurysm patients. Collagenous proteins were quantified by densitometry of autoradiograms obtained from SDS-PAGE of pepsin digested $^3$H-labeled media proteins. Only two patients, HR and ME, had a ratio of type I/III collagen which was greater than three standard deviations from the mean of both control values and those of other aneurysm patients. HR was a 70 year old male with an abdominal and popliteal aneurysm and ME was a 65 year old female with an abdominal and thoracic aneurysm. For neither patient could a clear family history of the disease be established.

mRNA Levels Coding for Procollagen

Decreased levels of type III collagen following pepsin digestion can result from a decreased expression of the type III procollagen gene. To test whether the decreased levels of type III collagen in the media of these two fibroblast strains were the result of decreased steady state levels of mRNA, the ratios of mRNA coding for type I and III procollagen were measured. Northern blot analysis revealed 4.8 and 5.4 Kb type III procollagen transcripts in both control and patient samples [(FIG. 2)]. Northern blot analysis with the alpha1(I) cDNA probe detected 4.8 and 5.8 Kb transcripts. These multiple molecular weight mRNAs are characteristic of the procollagen transcripts of cultured skin fibroblasts. The relative ratio of mRNA coding for type I and III procollagen was examined by slot blot quantitation of poly A+ mRNA. The ratio of alpha1(I)-/alpha1(III) procollagen mRNA in the control cells was 5.0, comparable to published ratios for these mRNAs from normal cultured skin fibroblasts (Aumailley et al., 1988). The ratios for these two mRNAs were 5.8 in ME and 8.3 in HR fibroblasts, indicating no marked decrease in the steady state levels of mRNA coding for type III procollagen in the aneurysm patients compared to the control [(FIG. 2)].

Intracellular Protein Levels

Normal mRNA levels coupled with decreased media type III collagen following pepsin digestion means that either the translation rate of the mRNA coding for type III procollagen is reduced or that the protein is susceptible to in vivo enzymatic degradation intracellularly or after secretion into the media. In vitro pepsin digestion would also degrade structurally abnormal type III collagen. Examination of intracellular procollagen synthesis (without pepsin digestion) showed that the intracellular level of type III procollagen in ME fibroblasts was decreased compared to that of control fibroblasts and fibroblasts of other aneurysm patients [(FIG. 3)]. [FIG. 4 shows a] A comparison was made of media type procollagen secreted by ME and control (C) fibroblasts. Labeling of ME fibroblasts at 32° C. (instead of 37° C.) to minimize proteolysis of structurally abnormal type III procollagen molecules (*Superti-Furga and Steinman,* 1988) did not result in detectable increases in the synthesis or secretion of type III procollagen. Preliminary results from cell free translation of poly A+ mRNA suggest that the primary defect in this patient may involve a decrease in the translational efficiency of type III procollagen mRNA.

HR fibroblasts, by contrast, had apparently normal intracellular type III procollagen levels [(FIG. 3)].

Alterations in the Thermal Stability of Type III Collagen

Normal levels of intracellular type III procollagen in HR fibroblasts suggested that the cells synthesized and secreted a type III procollagen containing an alteration in the triple helical portion of the molecule, which rendered it sensitive to digestion by pepsin. To examine this further, we tested the triple helical stability of the type III collagen by rapid digestion of media proteins with a combination of trypsin and alpha-chymotrypsin for brief incubation periods at temperatures ranging from 30° C.–42° C. (*Superti-Fruga and Steinman,* 1988). At the lower temperatures of digestion (30° C.–34° C.), the ratio of type I/III collagen in the HR media was comparable to the control ratio, indicating that the rate of synthesis and secretion of type III procollagen by HR fibroblasts was similar to that of control. At temperatures above 36° C., however, the amount of type III collagen in HR media was specifically decreased, indicating an altered thermal stability of the protein. Type III collagen from control media (4 controls were examined) was consistently resistant to enzymatic digestion at temperatures below 39° C. The type III procollagen synthesized by six other aneurysm patients was also assayed with trypsin and alpha-chymotrypsin digestion and demonstrated normal thermal stability.

[FIG. 6 is a] A densitometric tracing was made of four lanes of the incubation experiments set out above [in FIG. 5]. [Panel A is a densitometric tracing of the media collagen bands present after enzymatic digestion at 30° C. and panel B is a tracing of the media proteins after digestion at 36° C. The dotted line represents the tracing of the HR lanes and the solid line the control lanes.] Quantitation of the peaks demonstrated a specific reduction of over 50% in the type III collagen in HR media following digestion at 36° C. compared to digestion at 30° C. This altered thermal stability indicates that the triple helical confirmation of the type III collagen synthesized by HR fibroblasts is imperfect, probably as a result of an amino acid substitution in the triple helical domain of the molecule (*Superti-Furga et al.,* 1989; *Stolle et al.,* 1985; *Prockop et al.,* 1989; *Byers et al.,* 1990).

By contrast, no alteration in the thermal stability of the type III collagen secreted by ME cells was detected by digestion with trypsin and alpha-chymotrypsin digestion (5 minutes [FIG. 7]).

APPENDIUM OF REFERENCES

Aumailley M., Posel E., Martin G. R., Yamada Y., Muller P. K.: Low production of procollagen III by skin fibroblasts from patients with Ehlers Danlos syndrome type IV is not caused by decreased levels of procollagen III mRNA. *Eur. J. Clin. Invest.* 18:207-12, 1988.

Bengtsson H., Norrgard O., Angquist K. A., Ekberg O., Oberg L., Bergquist D.: Ultrasonographic screening of the abdominal aorta among siblings of patients with abdominal aortic aneurysms. *Br. J. Surg.* 76: 589-591, 1989.

Bruckner P., Prockop D. J.: Proteolytic enzymes as probes for the triple-helical conformation of procollagen. *Anal. Biochem.* 110:360-8, 1981.

Busuttil R. W., Abou-Zamzam A. M., Machleder H. I.: Collagenase activity of the human aorta. *Arch. Surg.* 115:1373-8, 1980.

Busuttil R. W., Rinderbriecht H., Flesher A., Carmack C.: Elastase activity: the role of elastase in aortic aneurysm formation. *J. Surg. Res.* 32:214-7, 1982.

Byers P., Mutations in collagen genes: Biochemical and phenotypic consequences. In: Extracellular Matrix Genes. ed. by Sandell L. J. and Boyd C. D., New York, N.Y., Academic press, 1990, pp. 251-263.

Chu M.-L., Myers J. C., Bernard MP, Ding J.-F., Ramirez F.: Cloning and characterization of five overlapping cDNAs specific for human pro alpha1(I)collagen chain. *Nuc. Acids Res.* 10:5925-34, 1982.

Cole C. W., Barber G. G., Bouchard A. G., McPhail N. V., Roberge C., Waddell W. G., Wellington J. L., Abdominal aortic aneurysm: consequences of a positive family history. *Can. J. Surg.* 32:117-20, 1989.

Darling R. C., Brewster D. C., Darling R. C., LaMuraglia G. M., Moncure A. C., Cambria R. P., Abbott W. M.: Are familial abdominal aortic aneurysms different? *J. Vasc. Surg.* 10:39-43, 1989.

Deak S. B., Nicholls A. C., Pope F. M., Prockop D. J.: The molecular defect in a nonlethal variant of osteogenesis imperfecta: synthesis of pro alpha2(I) chains which are not incorporated into trimers of type I procollagen. *J. Biol. Chem.* 258:15192-7, 1983.

Deak S. B., Van der Rest M., Prockop D. J.: Altered helical structure of a homotrimer of alpha1(I) chains synthesized by fibroblasts from a variant of osteogenesis imperfecta. *Collagen Rel. Res.* 5:305-13, 1985.

Fievez M.: Aneurysms and arterial dissections, in Camilleri J.-P., Colin L. B., Fiessinger J.-P., Bariety J. (eds): Diseases of the arterial wall. New York, N.Y., Springer-Verlag, 1989, pp. 533-545.

Johansen K., Koepsell T.: Familial tendency for abdominal aortic aneurysms. *JAMA* 256:1934-6, 1986.

Keeley F. W., Todorovich L., Rabinovitch M.: Elastin and elastase in the pathology of the arterial wall. In: Elastin and Elastases, Vol II, ed. by Robert L. and Hornbeck W., Boca Raton, Fla., CRC Press, 1989, pp. 169-184.

Kontusaari S., Tromp G., Kuivaniemi H., Ladda R. L., Prockop D. J.: Inheritance of an RNA splicing mutation (G +IVS20) in the type III procollagen gens (COL3AI) in a family with aortic aneurysms and easy bruisability. Phenotypic overlap between familial aneurysms and the Ehlers-Danlos syndrome type IV. *Am. J. Hum. Genet.* 47:112-120, 1990, a.

Kontusaari S., Tromp G., Kuivaniemi, Romanic A. M., Prockop D. J.: A mutation in the gene for type III procollagen (COL3AI) in a family with aorticaneurysms. *J. Clin. Res.* 86: 1465-1473, 1990, b.

Leblanc R., Lozano A. M., van der Rest M., Guttmann R. D.: Absence of collagen deficiency in familial cerebral aneurysms. *J. Neurosurg.* 70:837-40, 1989.

Menashi S., Campa J. S., Greenhalgh R. M., Powell J. T.: Collagen in abdominal aortic aneurysm: Typing, content and degradation. *J. Vasc. Surg.* 6:578-82, 1987.

Neil-Dwyer G., Bartlett J. R., Nicholls A. C., Narcisi P., Pope F. M.: Collagen deficiency and ruptured cerebral aneurysms. *J. Neurosurg.* 54:16-20, 1987.

Nicod P., Bloor C., Godfrey M., Hollister D., Pyeritz R. D., Dittrich H., Polikar R., Peterson K. L.: Familial aortic dissecting aneurysm. *J. Amer. Coll. Cardiol.* 1989;13:811-9.

de Paepe A., van Landegem W., de Keyset F., de Reuck: Association of multiple intracranial aneurysms and collagen type III deficiency. *Clin. Neurol. Neurosurg.* 90:53-6, 1988.

Pierce R. P., Glaug M., Greco R. S., Mackenzie J. W., Boyd C. D., Deak S. B.: Increased procollagen mRNA levels in carbon tetrachloride-induced liver fibrosis in rats. *J. Biol. Chem.* 262:1652-8, 1987.

Pope F. M., Narcisi P., Neil-Dwyer G., Nicholls A. C., Bartlett J., Doshi B.: Some patients with cerebral aneurysms are deficient in type III collagen. *Lancet* 1:973-5, 1981.

Pope F. M., Nicholls A. C., Dorrance D. E., Child A. H., Narcisi P.: Type III collagen deficiency and normal phenotype. *J. Royal Soc. Med.* 76:518-520, 1983.

Powell J. T., Greenhalgh R. M.: Multifactoral inheritance of abdominal aortic aneurysms. *Eur. J. Vasc. Surg.* 1:29-31, 1987.

Prockop D. J.: Mutations in collagen genes, consequences for rare and common diseases. *J. Clin. Invest.* 75:783-7, 1985.

Prockop D. J., Constantinou C. D., Dombrowski K. E., Hojima Y., Kadler K. E., Kuivaniemi H., Tromp G., Vogel B.: Type I Procollagen: The gene-protein system that harbors most of the mutations causing osteogenesis imperfecta and probably more common heritable disorders of connective tissue. *Am. J. Med. Genet.* 34:60–67, 1989.

Prockop D. J., Kivirikko K. I.: Heritable diseases of collagen. *N. Eng. J. Med.* 311:376–86, 1984.

Rizzo R. J., McCarthy W. J., Saryu N. D., Lilly M. P., Shively V. P., Flinn W. R., Yao J. S. T.: Collagen types and matrix protein content in human abdominal aortic aneurysms. *J. Vasc. Surg.* 10:365–73, 1989.

Stolle C. A., Pyeritz R. E., Myers J. C., Prockop D. J.: Synthesis of an altered type III procollagen in a patient with type IV Ehlers-Danlos syndrome. *J. Biol. Chem.* 260:1937–44, 1985.

Superta-Furga A., Gugler E., Gitzelmann R., Steinmann B.: Ehlers-Danlos syndrome type IV: A multi-exon deletion in one of the two COL3A1 alleles affecting structure, stability, and processing of type III procollagen. *J. Biol. Chem.* 263:6226–32, 1988.

Superti-Furga A., Steinmann B., Ramirez F., Byers P. H.: Molecular defects of type III procollagen in Ehlers-Danlos syndrome type IV. *Hum. Genetics* 82:104–8, 1989.

Superti-Furga A., Steinmann B.: Impaired secretion of type III procollagen in Ehlers-Danlos syndrome type IV fibroblasts: correction of the defect by incubation at reduced temperature and demonstration of subtle alterations in the triple-helical region of the molecule. *Biochem. Biophys. Res. Comm.* 150:140–7, 1988.

Tilson M. D., Seashore M. R.: Fifty families with abdominal aortic aneurysms in two or more first order relatives. *Amer. J. Surg.* 147:551–3, 1984.

Tilson M. D., Seashore M. R.: Human genetics of the abdominal aortic aneurysm. *Surg. Gyn. Obst.* 158:129–32, 1984.

Tilson M. D.: Decreased hepatic copper levels, a possible chemical marker for the pathogenesis of aortic aneurysms in man. *Arch. Surg.* 117:1212–3, 1982.

Tilson M. D.: Atherosclerosis and aneurysm disease. *J. Vasc. Surg.* 12:371–2, 1990.

Tromp G., Kuivaniemi H., Shikata H., Prockop D. J.: A single base mutation that substitutes serine for glycine of the alpha1(III) chain of type III procollagen exposes an arginine and causes Ehlers-Danlos syndrome IV. *J. Biol. Chem.* 264:1349–52, 1989.

Zarins C. K., Glagov S.: Aneurysms and obstructive plaques: Differing local responses to atherosclerosis. In: Aneurysms, Diagnosis and Treatment, ed. by Bergan J. J. and Yao J. S. T., New York, N.Y., Grune and Stratton, 1982, pp. 61–82.

Zatina M. A., Zarins C. K., Gewertz B. L., Glagov S.: Role of medial lamellar architecture in the pathogenesis of aortic aneurysms. *J. Vasc. Surg.* 1:442–8, 1984.

The invention being thus described, it will be obvious that the same may be varied in many ways. Such variations are not to be regarded as a departure from the spirit and scope of the invention and all such modifications are intended to be included within the scope of the following claims.

We claim:

1. A method for diagnosing for an abdominal aortic aneurysm in a patient which comprises the steps of:
   (a) explanting a skin section containing dermal fibroblasts from the patient to a culture medium;
   (b) culturing the fibroblasts to confluence in the culture medium;
   (c) incubating the cultured fibroblasts with labeled proline to provide labeled procollagen in the culture medium;
   (d) separating the culture medium from the labeled procollagen and treating the labeled procollagen with a solution of protease inhibitor;
   (e) separating and purifying the labeled procollagen from the solution of protease inhibitor;
   (f) subjecting the labeled procollagen to protease digestion specific for non-collagenous proteins to form a collagenous mixture;
   (g) analyzing the collagenous mixture for the ratio of type I collagen to type III collagen;
   (h) analyzing a control collagenous mixture for the ratio of type I collagen to type III collagen; and
   (i) comparing the ratio of type I collagen to type III collagen in the collagenous mixture of step (g) to the control mixture of step (h), respectively.

2. The method according to claim 1, wherein the labeled proline in step (c) is $^3$H-proline.

3. The method according to claim 1, wherein the protease inhibitor in step (d) is selected from the group consisting of N-ethylmaleimide and p-aminobenzamidine.

4. The method according to claim 1, wherein the labeled procollagen is separated from the solution of protease inhibitor in step (e) by precipitation with ammonium sulfate, centrifugation, and dialysis.

5. The method according to claim 1, wherein the labeled procollagen in step (f) is subjected to pepsin digestion.

6. The method according to claim 1, wherein the ratio of type I procollagen to type III procollagen in steps (g) and (h) is analyzed by denaturing polyacrylamide gel electrophoresis.

* * * * *